(12) United States Patent
Kim

(10) Patent No.: US 11,902,675 B2
(45) Date of Patent: Feb. 13, 2024

(54) MULTI-BAND OPTICAL FILTERING METHOD AND APPARATUS

(71) Applicant: KOREA ELECTROTECHNOLOGY RESEARCH INSTITUTE, Changwon (KR)

(72) Inventor: Sun Kwon Kim, Suwon (KR)

(73) Assignee: KOREA ELECTROTECHNOLOGY RESEARCH INSTITUTE, Changwon (KR)

( * ) Notice: Subject to any disclaimer, the term of this patent is extended or adjusted under 35 U.S.C. 154(b) by 33 days.

(21) Appl. No.: 17/606,407

(22) PCT Filed: Sep. 2, 2020

(86) PCT No.: PCT/KR2020/011754
§ 371 (c)(1),
(2) Date: Oct. 25, 2021

(87) PCT Pub. No.: WO2021/091060
PCT Pub. Date: May 14, 2021

(65) Prior Publication Data
US 2022/0303508 A1      Sep. 22, 2022

(30) Foreign Application Priority Data

Nov. 8, 2019 (KR) .......................... 10-2019-0142587

(51) Int. Cl.
*H04N 25/11* (2023.01)
*G02B 26/02* (2006.01)
*A61B 3/12* (2006.01)

(52) U.S. Cl.
CPC ............. *H04N 25/11* (2023.01); *G02B 26/02* (2013.01); *A61B 3/12* (2013.01)

(58) Field of Classification Search
None
See application file for complete search history.

(56) References Cited

U.S. PATENT DOCUMENTS

| | | | |
|---|---|---|---|
| 2008/0084508 A1* | 4/2008 | Cole | H04N 5/275 348/744 |
| 2013/0301004 A1* | 11/2013 | Kahn | A61B 3/12 351/246 |

(Continued)

FOREIGN PATENT DOCUMENTS

| | | | | |
|---|---|---|---|---|
| CN | 102460270 A | * | 5/2012 | G02B 26/00 |
| EP | 1477103 A1 | * | 11/2004 | A61B 1/00009 |

(Continued)

OTHER PUBLICATIONS

English translation of CN-102460270-A Sharp, May 2012 (Year: 2012).*

*Primary Examiner* — James M Hannett

(57) ABSTRACT

The present invention relates to a multi-band optical filtering method and apparatus and to a multi-band optical filtering method and apparatus capable of filtering wavelengths of two or more bands in order to create a multi-wavelength image of a subject. In the present invention, the optical filtering apparatus for creating a multi-wavelength image of a subject comprises a filter unit having a plurality of sub filter units comprising a first sub filter unit through which a first wavelength band passes and a second sub filter unit through which a second wavelength band, which is different from the first wavelength band, passes, wherein while the light generated in a light source passes through the filter unit, the filter unit filters the light such that an intensity of the first wavelength band is dominant in a first region, and an intensity of the second wavelength band is dominant in a second region.

9 Claims, 17 Drawing Sheets

(56) References Cited

U.S. PATENT DOCUMENTS

2014/0218511 A1* 8/2014 Lee .................. G01J 3/505
                                                                                                     348/135
2016/0370565 A1   12/2016 Bredno et al.

FOREIGN PATENT DOCUMENTS

| | | | |
|---|---|---|---|
| JP | 2016527549 | A | 9/2016 |
| KR | 950005008 | A | 2/1995 |
| KR | 10-0199982 | B1 | 6/1999 |
| KR | 10-2017-0062830 | A | 6/2017 |
| KR | 101798215 | B1 | 11/2017 |
| KR | 20190075795 | A | 7/2019 |
| WO | WO-9416622 | A1 * | 8/1994 ............. A61B 5/444 |
| WO | WO2019124739 | A1 | 6/2019 |

* cited by examiner

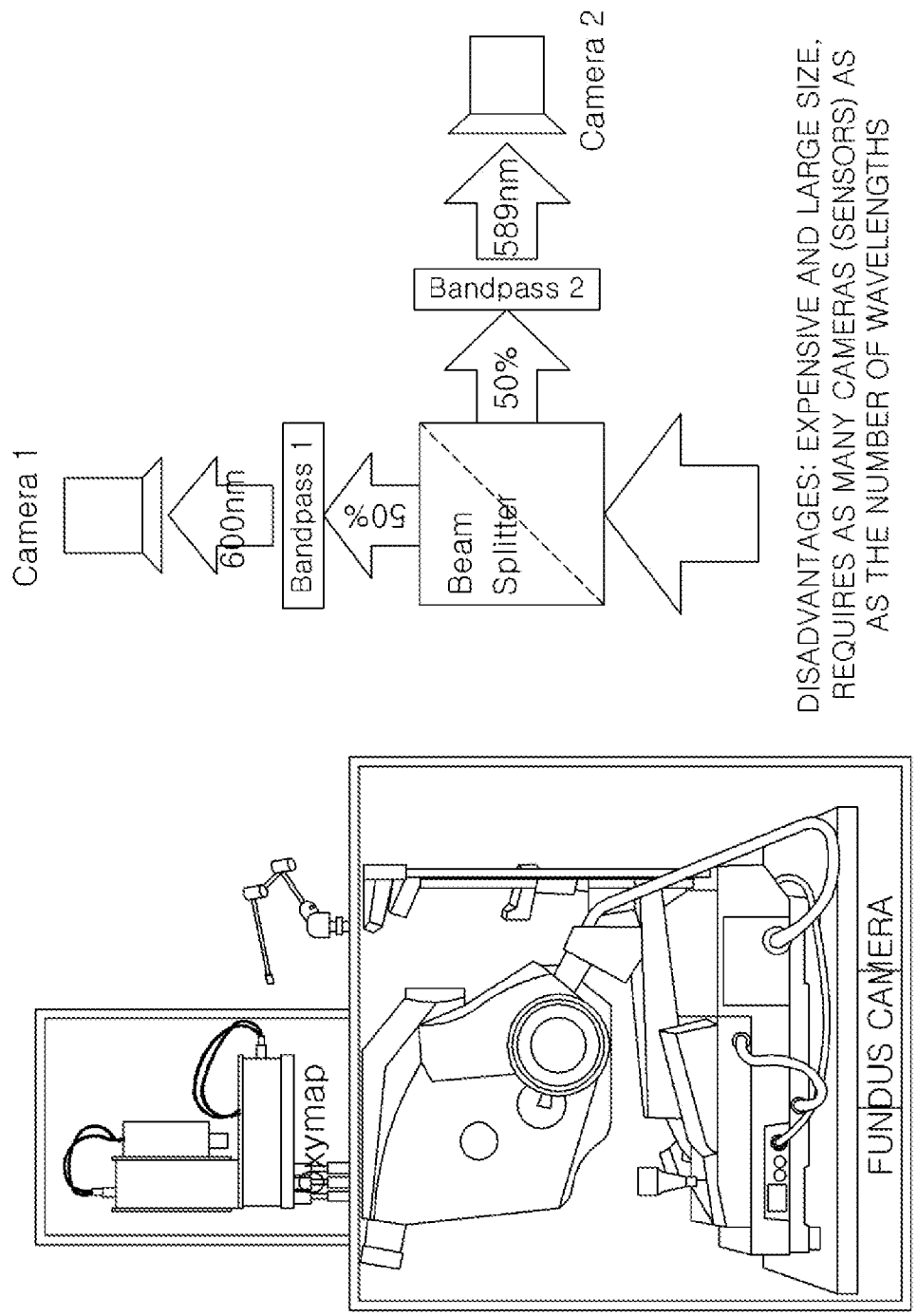

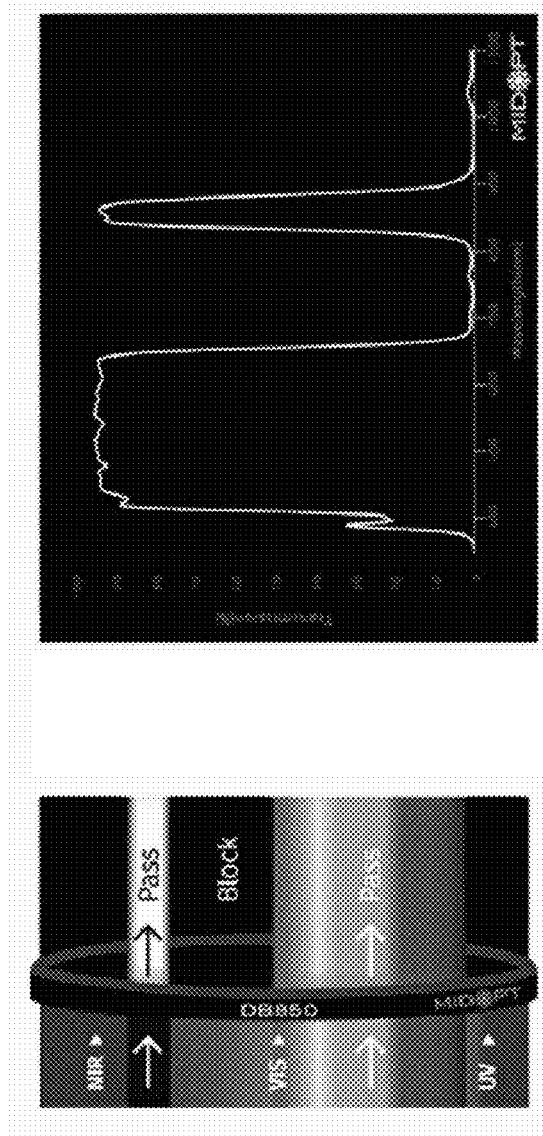

FIG. 1B

METHOD USING DUAL BANDPASS FILTER THROUGH WHICH ONLY TWO WAVELENGTHS PASS

DISADVANTAGES: WIDTH OF PASSING WAVELENGTH IS WIDER THAN THAT OF FILTER THROUGH WHICH ONE WAVELENGTH PASSES(100 TO 300nm)
→FIELD OF APPLICATION IS LIMITED, AND RESPONSE TO RESPONSE TO SPECIFIC WAVELENGTH IS LOW

*WAVELENGTH WIDTH (FWHM) OF TYPICAL BANDPASS FILTER THROUGH WHICH ONLY ONE WAVELENGTH PASSES IS ABOUT 5 TO 10nm

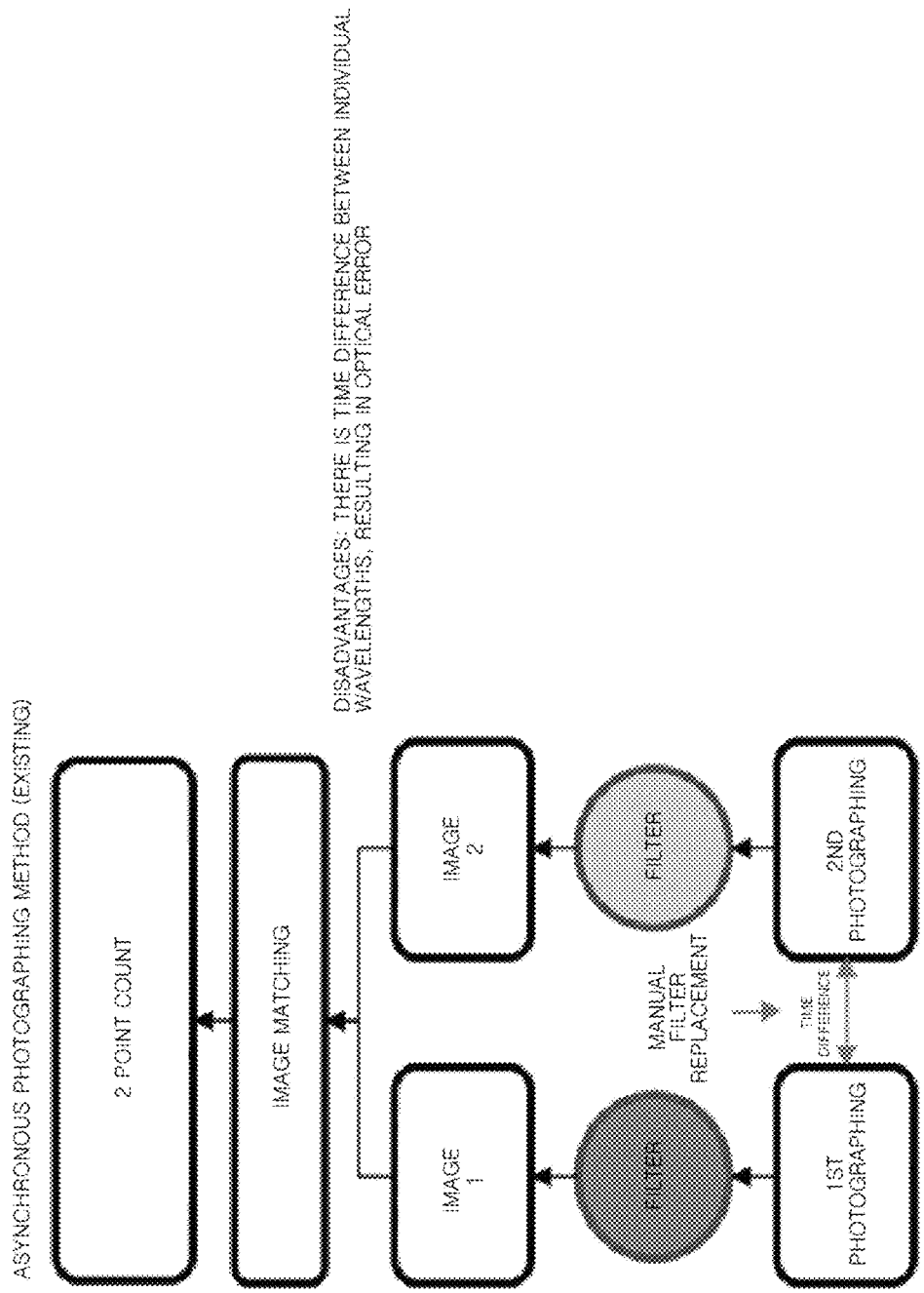

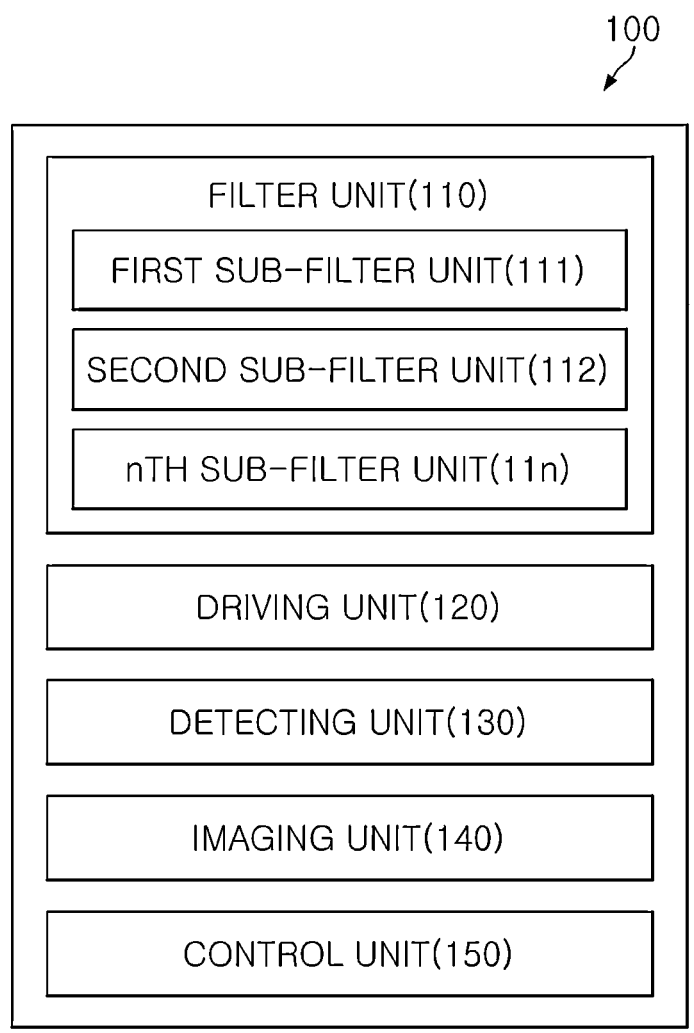

(a)  (b)

MULTI-BAND OPTICAL FILTERING METHOD AND APPARATUS

CROSS-REFERENCE TO RELATED APPLICATION

This application is a national stage application, filed under 35 U.S.C. § 371, of International Patent Application No. PCT/KR2020/011754, filed on Oct. 25, 2021, which claims the priority of Korean application No. 10-2019-0142587 filed Nov. 8, 2019, the contents of which are incorporated by reference.

TECHNICAL FIELD

The disclosure relates to a method and an apparatus for multi-band optical filtering and, more specifically, to a method and an apparatus for multi-band optical filtering, wherein in order to generate a multi-wavelength image regarding a subject, wavelengths in two or more of multiple bands can be filtered.

BACKGROUND ART

There exist various applications that need to acquire optical information regarding two or more of multiple bands from a subject.

For example, a retinal camera for diagnosing lesions of eyeballs acquires optical images in two wavelengths (569 nm, 600 nm) so as to measure the oxygen saturation of blood that flows through blood vessels in eyeballs.

Conventional methods employed to this end are as follows: in order to acquire optical information (images or signals) in two or more of multiple narrowband wavelengths, a beam splitter (BS) is commonly used, a filter is configured by using a special material that transmits multiple wavelengths, or multiple images are captured in respective wavelengths and then undergo registration through an algorithm or the like.

FIG. 1A illustrates a more specific example in which, in order to obtain two-wavelength optical information, a BS is used to separate a single subject image into two, and respective images pass through different narrowband optical filters.

In addition, FIG. 1B illustrates an exemplary scheme in which a dual band pass filter is used to transmit two wavelengths.

In addition, FIG. 1C illustrates an exemplary scheme in which two images are captured in respective wavelengths while replacing a narrowband optical filter, and the two images undergo registration by using software or the like.

Various other technologies are used as follows: one uses a principle according to which, if multiple devices use distance-measuring image sensors and are in focus, the subject is at the focal distance, and if out of focus, the subject is away from the focal distance; another technology rotates a filter/mirror that reflects or transmits three partial wavelengths and reproduces an image synchronized with the rate of rotation thereof such that a single color moving image appears to human eyes.

However, in the case of FIG. 1A, a BS is necessary, and imaging systems (for example, cameras) are necessary as many as the number of narrowband wavelengths, thereby posing a problem in that costs rise, and the structural size increases.

In addition, in the case of FIG. 1B, the width of the wavelength that passes through the dual band pass filter is wider than general filters, and there is a limitation in that the dual band combination is very limited, depending on the material.

In addition, in the case of FIG. 1C, images need to be captured successively as many as the number of narrowband wavelengths, and there is a problem in that errors may occur depending on movements of the subject or the imaging system in time intervals in which images are captured.

DISCLOSURE OF INVENTION

Technical Problem

The disclosure has been made to solve the above-mentioned problems occurring in the prior art, and it is an aspect of the disclosure to provide a method and an apparatus for multiband optical filtering, wherein an apparatus capable of filtering wavelengths in two or more of multiple bands in order to generate a multiwavelength image regarding a subject can be implemented in a compact size and at a reduced cost, and can also be attached to existing optical equipment such that the same is endowed with a selective optical filtering performance.

Other detailed aspects of the disclosure will be clearly identified and understood from the following detailed description by experts or researchers in the pertinent technical field.

Solution to Problem

An optical filtering apparatus according to an embodiment of the disclosure is an optical filtering apparatus for generating a multi-wavelength image of a subject, the optical filtering apparatus including: a filter unit configured to have a plurality of sub-filter units including a first sub-filter unit through which a first wavelength band passes and a second sub-filter unit through which a second wavelength band, which is different from the first wavelength band, passes, wherein, while light generated in a light source passes through the filter unit, the filter unit filters the light such that an intensity of the first wavelength band is dominant in a first region and an intensity of the second wavelength band is dominant in a second region.

The optical filtering apparatus may further include: a driving unit configured to drive the filter unit, wherein the driving unit drives the filter unit such that the intensity of the first wavelength band is dominant in the first region at a first time point, the intensity of the second wavelength band is dominant in the first region at a second time point, and an nth wavelength band corresponding to the plurality of sub-filter units is sequentially dominant in the first region at a subsequent nth time point.

The driving unit may drive the filter unit to rotate about a rotation axis.

In addition, the optical filtering may further include: an imaging unit configured to generate an image of the subject, wherein the imaging unit generates the multi-wavelength image of the subject by using one or two or more among a plurality of subject images generated at a plurality of time points including a first subject image generated at the first time point and a second subject image generated at the second time point.

The imaging unit may separate a 1-1-th wavelength image corresponding to the first wavelength band and a 1-2-th wavelength image corresponding to the second wavelength band from the first subject image generated at the first time point, separate a 2-1-th wavelength image corresponding to the first wavelength band and a 2-2-th wavelength image corresponding to the second wavelength band from the second object image generated at the second time point, and then generate a first wavelength correction image corrected using the 1-1-th wavelength image and the 2-1-th wavelength image, and generate a second wavelength correction image corrected using the 1-2-th wavelength image and the 2-2-th wavelength image.

In addition, a gradient in which the intensity of the second wavelength band increases while the intensity of the first wavelength band decreases may be included between the first region and the second region.

In addition, the imaging unit may separate the 1-1-th wavelength image corresponding to the first wavelength band and the 1-2-th wavelength image corresponding to the second wavelength band from the first subject image generated at the first time point, and then generate a first wavelength correction image and a second wavelength correction image by correcting the intensity according to the gradient.

In addition, the driving unit may drive the filter unit to generate a composite wavelength image in which the first wavelength band and the second wavelength band are uniformly exposed and mixed while the filter unit rotates one or more turns, and the imaging unit may separate and generate a first wavelength correction image and a second wavelength correction image from the composite wavelength image.

In addition, the driving unit may drive the filter unit to move in one or two or more linear directions among vertical, horizontal, and oblique directions.

In addition, the first sub-filter unit may include a 1-1-th sub-filter piece and a 1-2-th sub-filter piece, the second sub-filter unit may include a 2-1-th sub-filter piece and a 2-2 sub-filter piece, and the 1-1-th sub-filter piece and the 1-2-th sub-filter piece may be positioned to cross each other with the 2-1-th sub-filter piece and the 2-2-th sub-filter piece.

Furthermore, the driving unit may include a gear train having a driving motor and a plurality of gears, and the number of rotations of the filter unit may be greater than the number of rotations of the driving motor by the gear ratio of the gear train.

In addition, an optical filter method according to another embodiment of the disclosure is an optical filter method for generating a multi-wavelength image of a subject, the method including: filtering light generated from a light source using a filter unit configured to have a plurality of sub-filter units including a first sub-filter unit through which a first wavelength band passes and a second sub-filter unit through which a second wavelength band, which is different from the first wavelength band, passes; and generating a multi-wavelength image of the subject using the light filtered by the filter unit, wherein, in the filtering, the filter unit filters and transmits the light such that an intensity of the first wavelength band is dominant in a first region, an intensity of the second wavelength band is dominant in a second region, and a gradient exists between the first region and the second region so as to have a gradual intensity change from the first wavelength band to the second wavelength band.

Advantageous Effects of Invention

A method and an apparatus for multiband optical filtering according to an embodiment of the disclosure are advantageous in that an apparatus capable of acquiring band optical information regarding two or more of multiple wavelengths can be implemented, based on a mechanical driving scheme, in a compact size and at a reduced cost, and can be used to endow existing optical equipment with a selective optical filtering performance.

BRIEF DESCRIPTION OF DRAWINGS

The accompanying drawings, which are included as part of the detailed description to help the understanding of the disclosure, provide embodiments of the disclosure, and together with the detailed description, explain the technical spirit of the disclosure.

FIGS. 1A to 1C are diagrams illustrating a multi-wavelength imaging apparatus according to the related art.

FIG. 2 is a block diagram illustrating an optical filtering apparatus according to an embodiment of the disclosure.

BEST MODE FOR CARRYING OUT THE INVENTION

Figure 3:
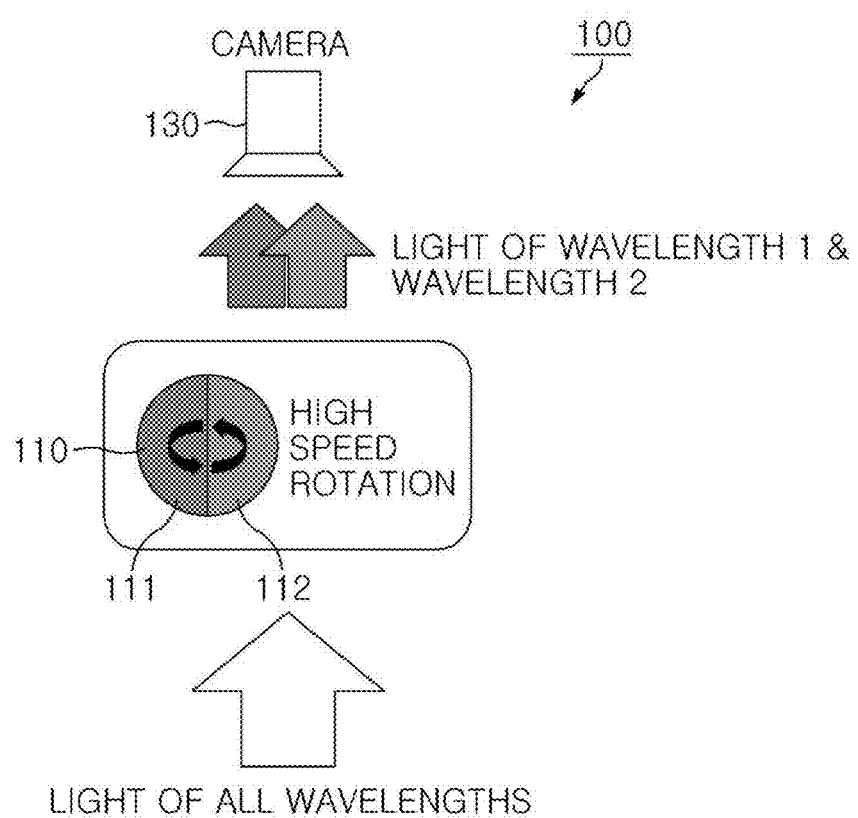
FIGS. 3 to 6, 7A, 7B, 8A, 8B, 9A, 9B, 10A and 10B are specific embodiments of an optical filtering apparatus according to an embodiment of the disclosure.

The disclosure may have various modifications and various embodiments. Hereinafter, specific embodiments will be described in detail with reference to the accompanying drawings.

The following embodiments are provided to help a comprehensive understanding of the method, apparatus, and/or system described herein. However, this is merely an example and the disclosure is not limited thereto.

In describing the embodiments of the described technology, when it is determined that a detailed description of known technologies related to the described technology may unnecessarily obscure the subject matter of the described technology, a detailed description thereof will be omitted. In addition, terms to be described later are terms defined in consideration of functions in the described technology, which may vary according to the intention or custom of users or operators. Therefore, the definition should be made on the basis of contents throughout this specification. The terms used in the detailed description are only for describing the embodiments of the described technology and should not be construed as limiting. Unless explicitly used otherwise, expressions in the singular form include the meaning of the plural form. In this description, expressions such as "comprising" or "including" are intended to refer to certain features, numbers, steps, actions, elements, and some or combination thereof, and should not be construed as excluding the presence or possibility of one or more other features, numbers, steps, actions, elements, and some or combination thereof other than those described.

In addition, terms such as first, second, etc., may be used to describe various elements, but the elements are not limited by the terms, and the terms are used only for the purpose of distinguishing one element from other elements.

Hereinafter, exemplary embodiments of an optical filtering method and apparatus 100 according to an embodiment of the disclosure will be described with reference to the accompanying drawings.

First, in FIG. 2, the configuration of the optical filtering apparatus 100 according to an embodiment of the disclosure is described.

As can be seen in FIG. 2, the optical filtering apparatus 100 according to an embodiment of the disclosure may generate a multi-wavelength image of a subject, and may include a filter unit 110 having a plurality of sub-filter units including a first sub-filter unit 111 through which a first wavelength band passes and a second sub-filter unit 112 through which a second wavelength band, which is different from the first wavelength band, passes.

In this case, in the optical filtering apparatus 100 according to an embodiment of the disclosure, while light generated in a light source passes through the filter unit 110, the filter unit filters the light such that an intensity of the first wavelength band is dominant in a first region, and an intensity of the second wavelength band is dominant in a second region.

Here, that the intensity of the first wavelength band is dominant means that the intensity of the first wavelength band is sufficiently stronger than the intensity of other wavelength bands so that the characteristic of the first wavelength band mainly appears.

Figure 4:
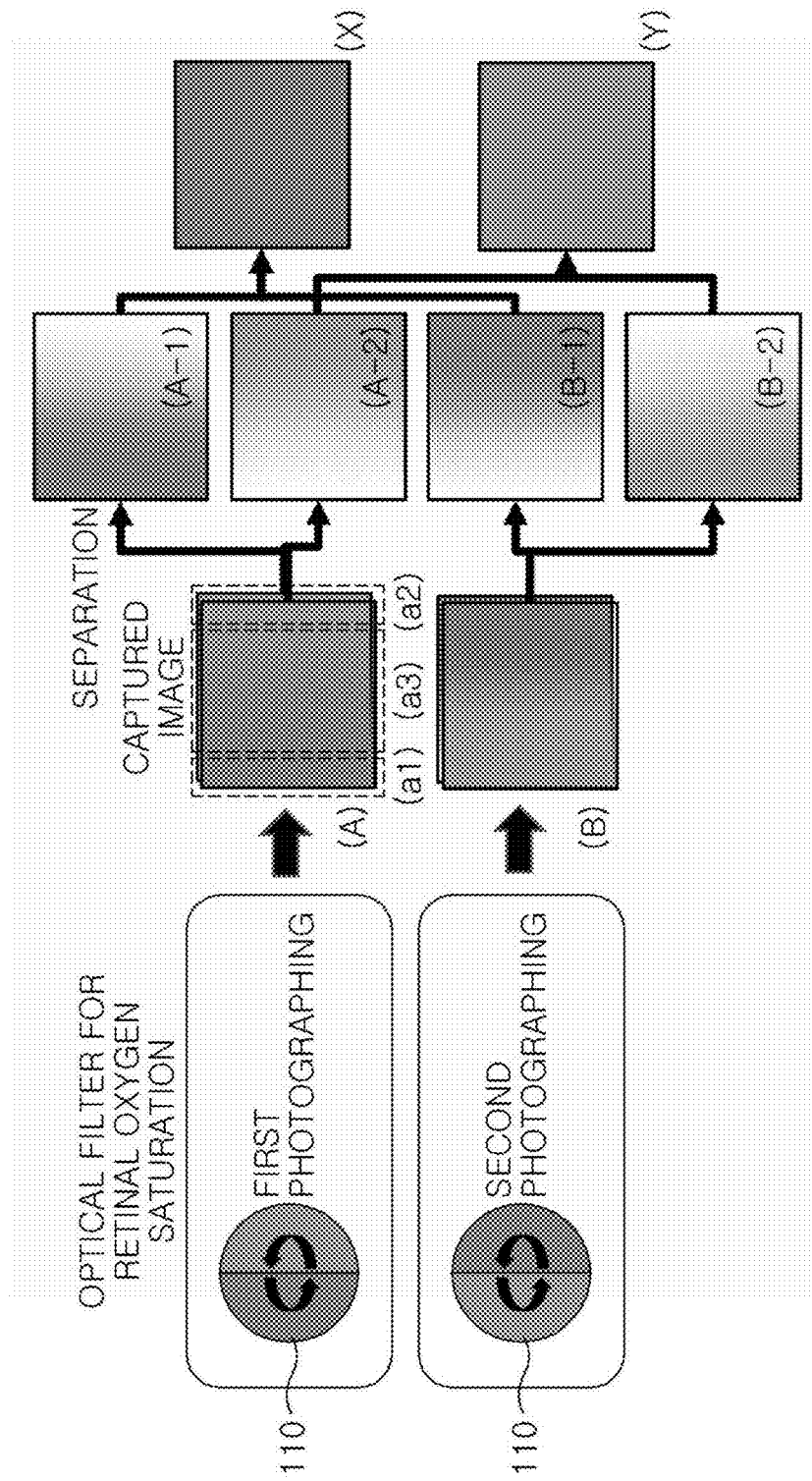

For a more specific example, in a region a1 of FIG. 4, the intensity of the first wavelength band of red (R) is dominant, and in a region a2 of FIG. 4, the intensity of the second wavelength band of green (G) is dominant.

In addition, a gradient in which the intensity of the second wavelength band increases while the intensity of the first wavelength band decreases may be included between the first region and the second region.

For a more specific example, in FIG. 4, it can be seen that a region a3 between the region a1 and the region a2 has a gradient in which the intensity is gradually changed from the first wavelength band of the red (R) to the second wavelength band of the green (G).

As described above, in the optical filtering apparatus 100 according to an embodiment of the disclosure, while the light generated from the light source passes through the filter unit 110, the filter unit 110 filters the light such that an intensity of the first wavelength band is dominant in a first region and an intensity of the second wavelength band is dominant in a second region.

In addition, as can be seen in FIG. 2, the optical filtering apparatus 100 according to an embodiment of the disclosure may further include a driving unit 120 configured to drive the filter unit 110, a detecting unit 130 configured to detect light passing through the filter unit 110 and being emitted to a subject, an imaging unit 140 configured to generate an image of the subject, and a control unit 150 configured to control the driving of the filter unit 110.

However, the disclosure is not limited thereto, and in the disclosure, the configuration of some or all of the driving unit 120, the detecting unit 130, the imaging unit 140, and the control unit 150 is removed or modified to constitute the optical filtering apparatus 100 according to the disclosure.

More specifically, in the optical filtering apparatus 100 according to an embodiment of disclosure, the driving unit 120 may drive the filter unit 110 such that the intensity of the first wavelength band is dominant in the first region at a first time point, the intensity of the second wavelength band is dominant in the first region at a second time point, and an nth wavelength band corresponding to the plurality of sub-filter units is sequentially dominant in the first region at a subsequent nth time point.

At this time, as can be seen in FIG. 3, the driving unit 120 may drive the filter unit 110 to rotate around a rotation axis.

Accordingly, in FIG. 3, the driving unit 120 may rotate the filter unit 110, and thus, at a first time point, the intensity of the first wavelength band of red (R) passing through the first sub-filter unit 111 may be dominant in the first region, and at a subsequent second time point, the intensity of the second wavelength band of green (G) passing through the second sub-filter unit 112 may be dominant in the first region while the filter unit 110 rotates half a turn.

In addition, in the optical filtering apparatus 100 according to an embodiment of the disclosure, as can be seen in FIG. 3, the detecting unit 130 such as a camera may be provided, and accordingly, the detecting unit 130 may detect light that passes through the filter unit 110 and is emitted to a subject, to generate optical information such as an optical image.

In addition, in the optical filtering apparatus 100 according to an embodiment of the disclosure, the imaging unit 140 may generate the multi-wavelength image of the subject by using one or two or more among a plurality of subject images generated at a plurality of time points including a first subject image generated at the first time point and a second subject image generated at the second time point.

Accordingly, as can be seen in FIG. 3, the optical filtering apparatus 100 according to an embodiment of the disclosure relates to a technique for measuring or imaging light by transmitting light of two or more bands of wavelengths. Optical information such as images for two or more of multiple wavelength bands can be acquired based on a mechanical driving method, and the optical filtering apparatus 100 can be miniaturized and implemented at a low cost, and furthermore, the optical filtering apparatus 100 can be attached to the existing optical equipment to selectively provide optical filtering performance.

In this regard, various embodiments of the optical filtering apparatus 100 according to an embodiment of the disclosure are illustrated in FIGS. 4 to 10.

Hereinafter, the optical filtering apparatus 100 according to an embodiment of the disclosure is divided into components and is described in more detail with reference to FIGS. 4 to 10.

First, as can be seen in FIG. 4, in the optical filtering apparatus 100 according to an embodiment of the disclosure, the imaging unit 140 may separate a 1-1-th wavelength image corresponding to the first wavelength band and a 1-2-th wavelength image corresponding to the second wavelength band from the first subject image generated at the first time point, may separate a 2-1-th wavelength image corresponding to the first wavelength band and a 2-2-th wavelength image corresponding to the second wavelength band from the second object image generated at the second time point, and then may generate a first wavelength correction image corrected using the 1-1-th wavelength image and the 2-1-th wavelength image, and may generate a second wavelength correction image corrected using the 1-2-th wavelength image and the 2-2-th wavelength image.

More specifically, in FIG. 4, the imaging unit 140 may separate a 1-1-th wavelength image ((A-1) in FIG. 4) corresponding to the first wavelength band and a 1-2-th wavelength image ((A-2) in FIG. 4) corresponding to the second wavelength band from a first subject image ((A) in FIG. 4) generated at the first time point, and may separate the 2-1-th wavelength image ((B-1) in FIG. 4) corresponding to a first wavelength band and the 2-2-th wavelength image ((B-2) in FIG. 4) corresponding to the second wavelength band from a second subject image ((B) in FIG. 4) generated at the second time point.

Subsequently, the imaging unit 140 may generate a first wavelength correction image ((X) of FIG. 4) corrected using a 1-1-th wavelength image ((A-1) in FIG. 4) and a 2-1-th wavelength image ((B-1) in FIG. 4), and may generate a second wavelength correction image ((Y) of FIG. 4) corrected using a 1-2-th wavelength image ((A-2) in FIG. 4) and a 2-2-th wavelength image ((B-2) in FIG. 4)

Accordingly, in the optical filtering apparatus 100 according to an embodiment of the disclosure, as can be seen in FIG. 4, by generating the multi-wavelength image of the subject while driving the filter unit 110, it is possible to have an effect of photographing the image of the subject while replacing the filters of a plurality of wavelengths, and furthermore, it is possible to effectively prevent the occurrence of an error in the image due to the movement of the subject.

Figure 5:
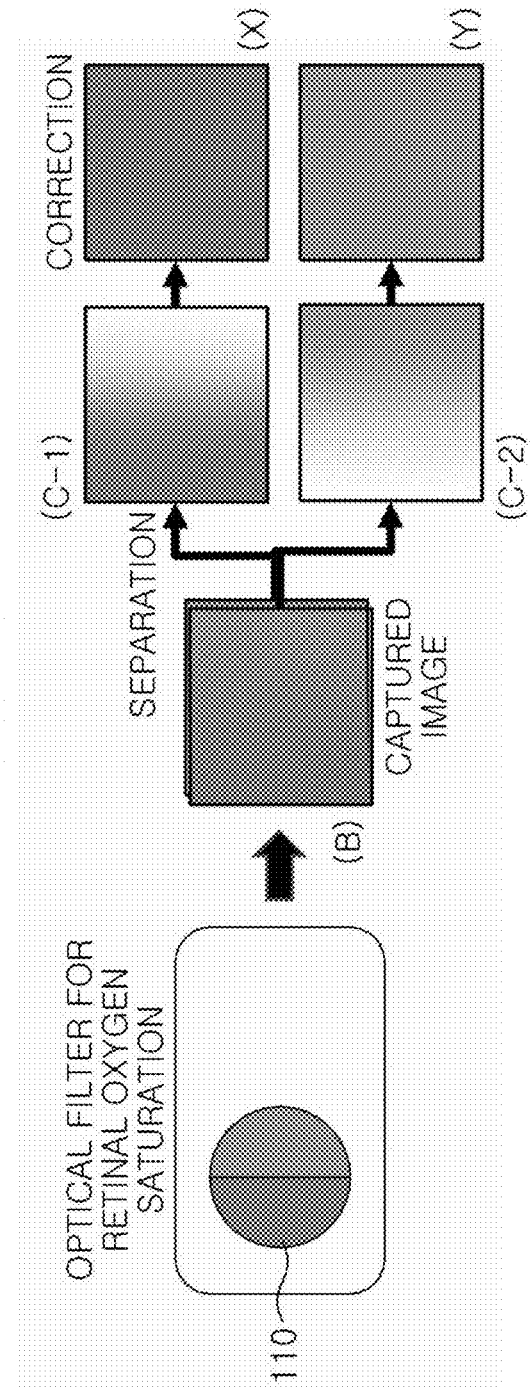

In addition, as can be seen in FIG. 5, in the optical filtering apparatus 100 according to an embodiment of disclosure, the imaging unit 140 may separate the 1-1-th wavelength image corresponding to the first wavelength band and the 1-2-th wavelength image corresponding to the second wavelength band from the first subject image generated at the first time point, and may then correct the intensity according to the gradient to generate a first wavelength correction image and a second wavelength correction image.

More specifically, in FIG. 5, the imaging unit 140 may separate a 1-1-th wavelength image ((C-1) in FIG. 5) corresponding to the first wavelength band and a 1-2-th wavelength image ((C-2) in FIG. 5) corresponding to the second wavelength band from a first subject image ((C) in FIG. 5) generated at the first time point, and may then correct the intensity according to the gradient to generate a first wavelength correction image ((X) in FIG. 5) and a second wavelength correction image ((Y) in FIG. 5).

Accordingly, in the optical filtering apparatus 100 according to an embodiment of the disclosure, as can be seen in FIG. 5, it is possible to generate the multi-wavelength image of the subject from one image captured in a state in which the filter unit 110 is not driven.

Furthermore, in the optical filtering apparatus 100 according to an embodiment of the disclosure, the first wavelength correction image and the second wavelength correction image generated in the embodiment of FIG. 4 and the embodiment of FIG. 5 may be compared to each other and verified, or an image with improved quality may be obtained by using the generated images.

Figure 6:
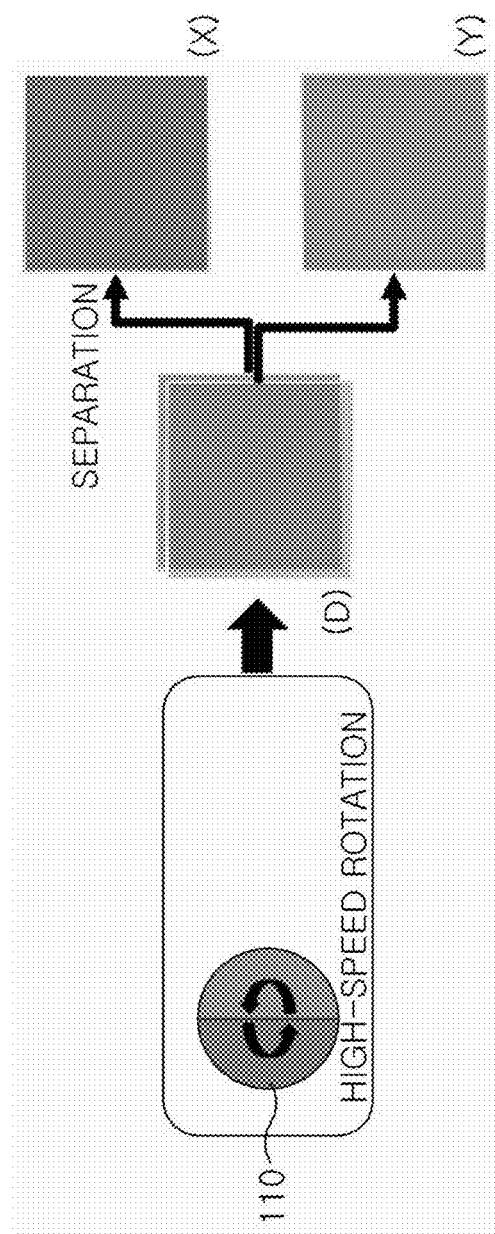
Figure 7:
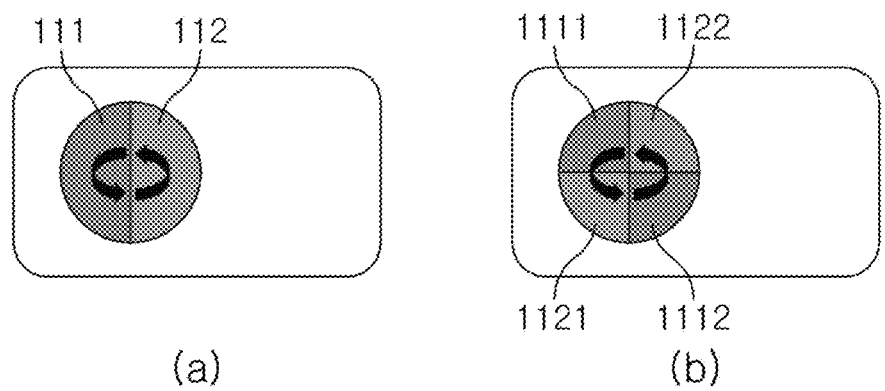
Figure 8:
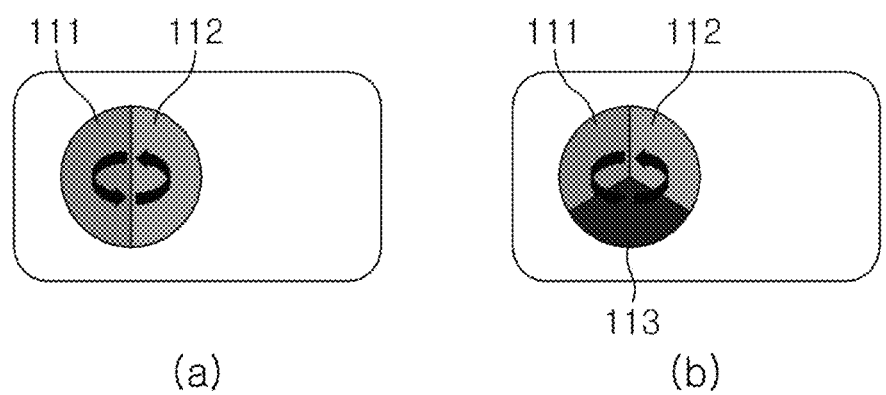
Figure 9:
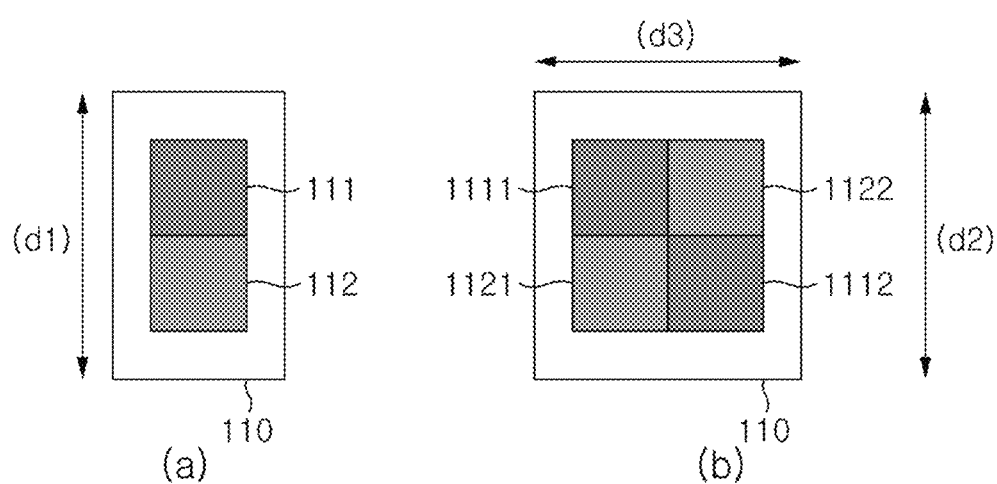
Figure 10:
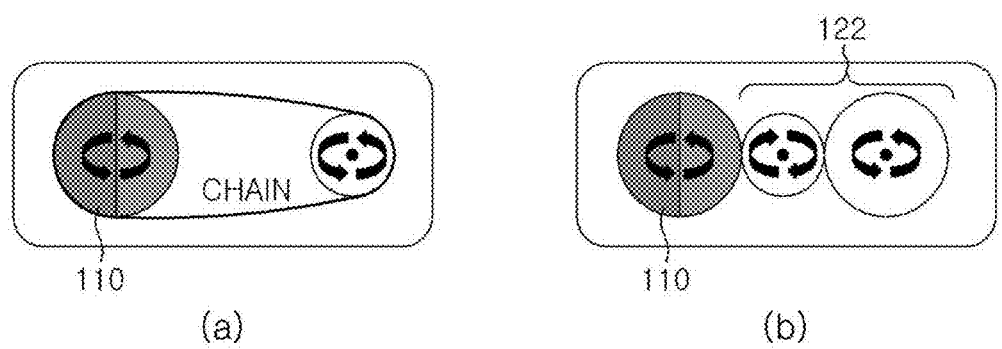

In addition, as can be seen in FIG. 6, in the optical filtering apparatus 100 according to an embodiment of the disclosure, the driving unit 120 may drive the filter unit 110 to generate a composite wavelength image in which the first wavelength band and the second wavelength band are uniformly exposed and mixed while the filter unit 110 rotates one or more turns, and thus the imaging unit 140 may separate and generate the first wavelength correction image and the second wavelength correction image from the composite wavelength image.

More specifically, in FIG. 6, the driving unit 120 may drive the filter unit 110 to generate a composite wavelength image ((D) in FIG. 6) in which the first wavelength band and the second wavelength band are uniformly exposed and mixed while the filter unit 110 rotates one or more turns, and thus the imaging unit 140 may separate and generate the first wavelength correction image ((X) in FIG. 6) and the second wavelength correction image ((Y) in FIG. 6) from the composite wavelength image ((D) in FIG. 6).

Accordingly, in the optical filtering apparatus 100 according to an embodiment of the disclosure, as can be seen in FIG. 6, it is possible to generate the multi-wavelength image of the subject from one image captured by exposing the detecting unit 130 such as a camera while driving the filter unit 110, thereby obtaining an image having more uniform signal-to-noise ratio (SNR).

Furthermore, in the optical filtering apparatus 100 according to an embodiment of the disclosure, the first wavelength correction image and the second wavelength correction image generated in the embodiments of FIGS. 4 to 6 are compared to each other and verified. Alternatively, it is possible to obtain an image with improved quality by using the generated images.

MODES FOR CARRYING OUT THE INVENTION

In addition, as can be seen in FIGS. 7A and 7B, in the filter unit 110 of the optical filtering apparatus 100 according to an embodiment of the disclosure, the first sub-filter unit 111 may include a 1-1-th sub-filter piece 1111 and a 1-2-th sub-filter piece 1112, and the second sub-filter unit 112 may include a 2-1-th sub-filter piece 1121 and a 2-2 sub-filter piece 1122. In this case, and the 1-1-th sub-filter piece 1111 and the 1-2-th sub-filter piece 1112 may be positioned to cross each other with the 2-1-th sub-filter piece 1121 and the 2-2-th sub-filter piece 1122.

That is, in the disclosure, when the filter unit 110 is divided into two to make an angle of 180 degrees per filter piece, the filter unit 110 may be rotated by 180 degrees (FIG. 7A) during a camera exposure time, and when the filter unit 110 is divided into four to make an angle of 90 degrees per filter piece, the filter unit 110 may be rotated by 90 degrees (FIG. 7B) during the camera exposure time.

Furthermore, when the filter unit 110 is divided into N equal parts to make an angle of 360 degrees/N per filter piece, the filter unit 110 may be rotated by 360 degrees/N during the camera exposure time, thereby generating the multi-wavelength image by a single captured image.

In this case, the minimum exposure time (sec) becomes an angle (°)/filter revolutions per second (°/sec) per filter piece (=(360°/N)/RPS), so that, by providing a plurality of filter pieces as shown in FIG. 7B, higher-speed photographing is also possible.

In addition, as can be seen in FIGS. 8A and 8B, in the optical filtering apparatus 100 according to an embodiment of the disclosure, the filter unit 110 may be divided by the number of wavelengths to be photographed at a time, so that the image for N wavelengths may be acquired by one photographing.

At this time, the filter unit 110 may be divided into N equal parts (111, 112, and 113 in FIGS. 8A and 8B) to make an angle of 360 degrees/N per filter, and by rotating the filter unit 110 by 360 degrees/N, it is possible to acquire a multi-wavelength image of N wavelengths by one photographing.

In this case, the minimum exposure time (sec) becomes an angle (°)/filter revolutions per second (°/sec) per filter (=(360°/N)/RPS), so that simultaneous photographing for N wavelengths is also possible.

In addition, as can be seen in FIGS. 9A and 9B, in the optical filtering apparatus 100 according to an embodiment of the disclosure, the filter unit 110 may be implemented in a circular shape as exemplified above. It is also possible to implement the filter unit 110 in various shapes such as linear or polygonal.

More specifically, as can be seen in FIG. 9A, in the filter unit 110, the first sub-filter unit 111 and the second sub-filter unit 112 may be implemented in a bar shape.

In this case, as can be seen in FIG. 9A, the driving unit 120 may generate the multi-wavelength image of the subject while driving the filter unit 110 up and down in a linear direction ((d1) in FIG. 9(a)).

In addition, as can be seen in FIG. 9B, in the filter unit 110, the first sub-filter unit 111 and the second sub-filter unit 112 may be implemented in a rectangular or polygonal shape.

In this case, as can be seen in FIG. 9B, the driving unit 120 may generate the multi-wavelength image of the subject while driving the filter unit 110 up and down or left and right ((d2) or (d3) in FIG. 9(b)) or driving the filter unit 110 in a linear direction such as diagonally.

In addition, as can be seen in FIGS. 10A and 10B, in the optical filtering apparatus 100 according to an embodiment of the disclosure, the driving unit 120 may drive the filter unit 110 using a chain (FIG. 10A) or may drive the filter unit 110 using a gear chain 122 (FIG. 10B).

When driving the filter unit 110 using the chain, it has the advantage that the disclosure can be implemented with a simple structure, and when driving the filter unit 110 using the gear train 122, the rotation can be made faster by adjusting the gear ratio of the gear train 122, and accordingly, the rotation speed of the filter unit 110 can be adjusted faster than the rotation speed of the driving motor 121.

Figure 11:
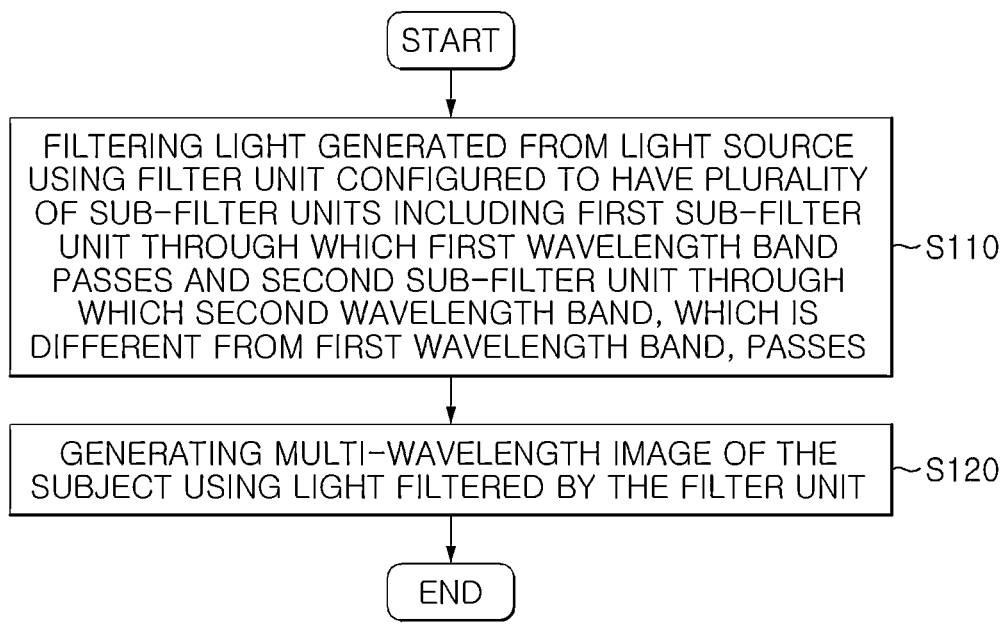
FIG. 11 is a flowchart illustrating an optical filtering method according to an embodiment of the disclosure.

In addition, FIG. 11 is a flowchart illustrating an optical filtering method according to an embodiment of the disclosure. As can be seen in FIG. 11, in an optical filtering method for generating a multi-wavelength image of a subject, the optical filtering method according to an embodiment of the disclosure may include filtering (S110) light generated from a light source using the filter unit 110 configured to have a plurality of sub-filter units including a first sub-filter unit 111 through which a first wavelength band passes and a second sub-filter unit 112 through which a second wavelength band, which is different from the first wavelength band, passes, and generating (S120) the multi-wavelength image of the subject using the light filtered by the filter unit 110, wherein, in the filtering (S110), the filter unit filters the light such that an intensity of the first wavelength band is dominant in a first region and an intensity of the second wavelength band is dominant in a second region.

In this case, for the optical filtering method according to an embodiment of the disclosure, since the description of the optical filtering apparatus 100 and FIGS. 2 to 10 may be referred to, repeated description will be omitted.

Figure 12:
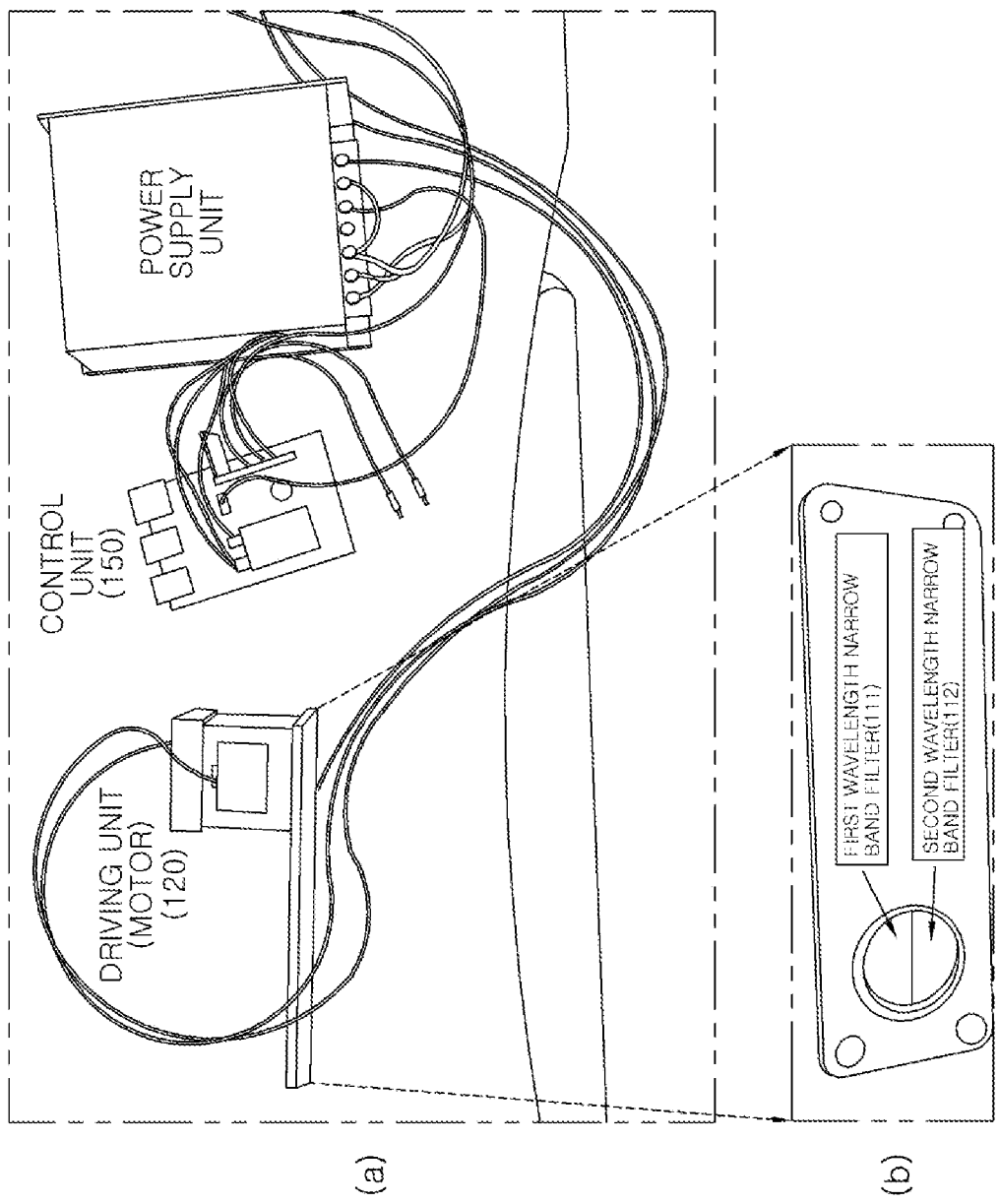
FIG. 12 is a sample photograph of an optical filtering apparatus according to an embodiment of the disclosure.

In addition, FIG. 12 illustrates a sample photograph of the optical filtering apparatus 100 according to an embodiment of the disclosure. As can be seen in FIG. 12, in the optical filtering apparatus 100 according to an embodiment of the disclosure, the filter unit 110 may include the first sub-filter unit 111 through which a first wavelength passes and the second sub-filter unit 112 through which a second wavelength passes.

In addition, the driving unit 120 may be configured using a motor, etc., and the control unit 130 may be configured using an electric circuit capable of controlling whether the motor is driven, speed, etc.

Figure 13:
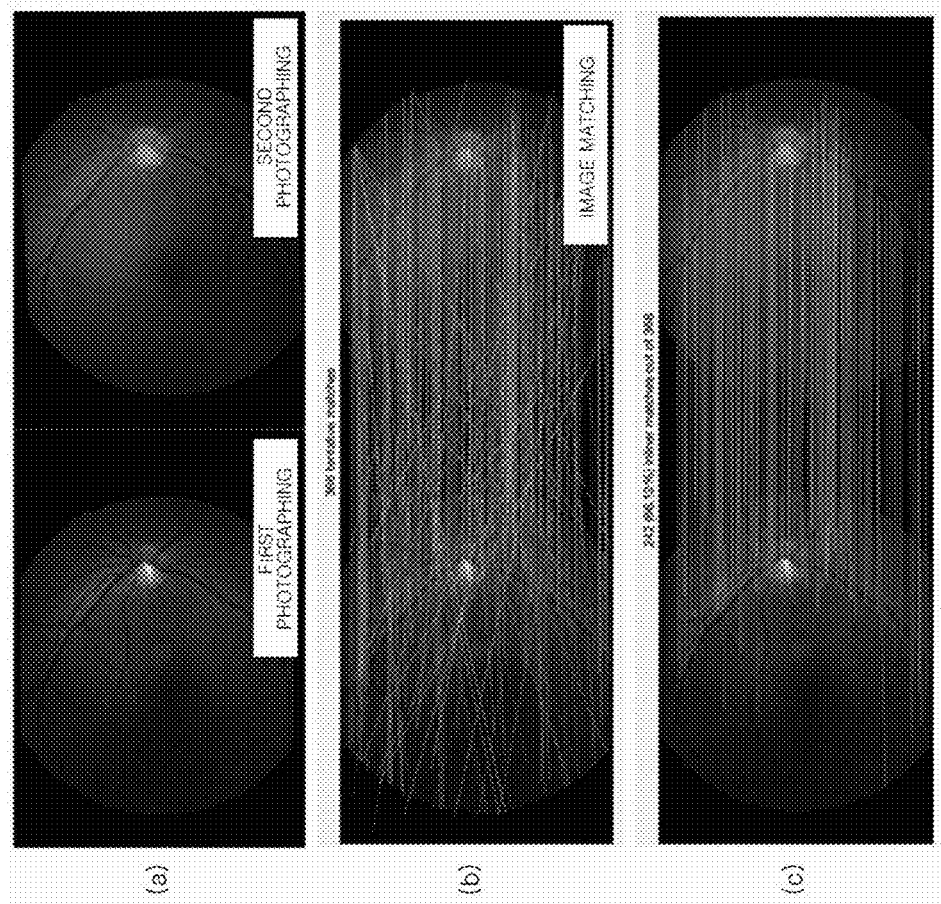
FIGS. 13A, 13B, 13C, 14 and 15 are diagrams illustrating a process of generating a multi-wavelength image in an optical filtering apparatus according to an embodiment of the disclosure.

Accordingly, in the optical filtering apparatus 100 according to an embodiment of the disclosure, as shown in FIGS. 13A to 13C, a first subject image may be captured at a first time point and a second subject image may be captured while the filter unit 110 is driven at a subsequent second time point (FIG. 13A), and then image matching may be performed on the first subject image and the second subject image (FIG. 13B and FIG. 13C), thereby generating a matched image of the subject.

More specifically, for example, in order to diagnose an eye lesion, a fundus camera may acquire optical images having two wavelengths (569 nm and 600 nm) to measure the oxygen saturation of blood flowing through the blood vessels inside the eye.

At this time, in the fundus camera, using the filter unit 110 including the first sub-filter unit 111 corresponding to the first wavelength (600 nm) and the second sub-filter unit 112 corresponding to the second wavelength (569 nm), a fundus image of the subject may be generated.

Figure 14:
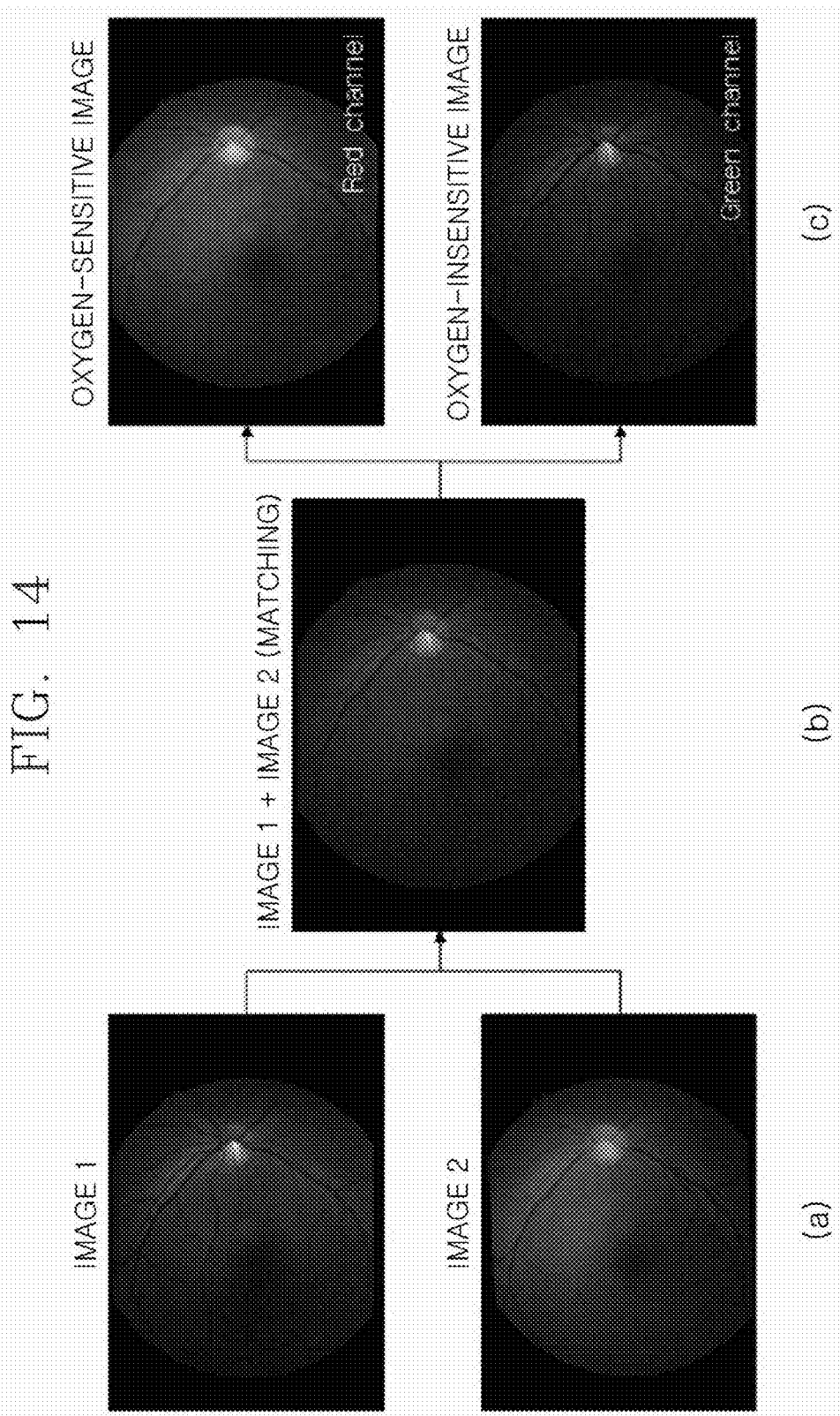

Accordingly, as can be seen in FIG. 14, in the fundus camera, a first subject image may be captured at the first time point, and a second subject image may be captured while the filter unit 110 is driven at a subsequent second time point ((a) in FIG. 14), and then an image obtained by matching the first subject image and the second subject image may be generated ((b) in FIG. 14), and from this, a first wavelength image (red channel) corresponding to the first wavelength 600 nm and a second wavelength image (green channel) corresponding to the second wavelength 569 nm may be generated ((c) in FIG. 14).

Figure 15:
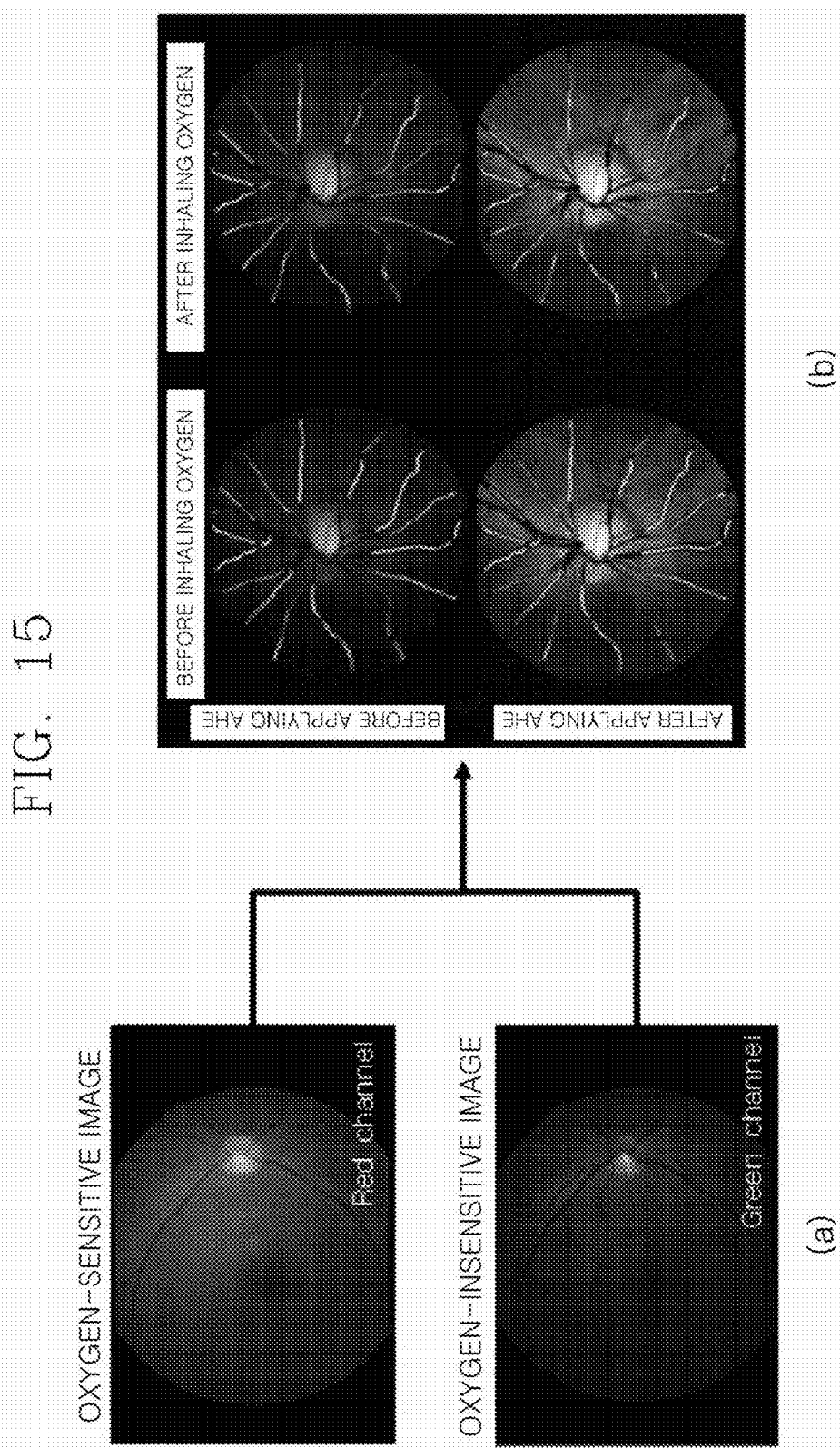

Subsequently, as can be seen in FIG. 15, in the fundus camera, using the first wavelength image (red channel) corresponding to the first wavelength 600 nm and the second wavelength image (green channel) corresponding to the second wavelength 569 nm, it is possible to obtain the multi-wavelength image showing the oxygen saturation of blood flowing through the blood vessels inside the eye of the subject ((b) in FIG. 15).

However, the disclosure is not necessarily limited thereto, and as described above, it is preferable to obtain the multi-wavelength image by a method more suitable for various subjects.

Accordingly, in the optical filtering apparatus 100 and method according to an embodiment of the disclosure, in order to generate a multi-wavelength image of a subject, an apparatus capable of filtering wavelengths in two or more of multiple bands may be miniaturized and may be implemented at a low cost. Furthermore, the apparatus can be attached to the existing optical equipment to provide selective optical filtering performance.

The above description is merely illustrative of the technical idea of the disclosure, and various modifications and variations are possible without departing from the essential characteristics of the disclosure by those skilled in the art to which the present invention pertains. Accordingly, the embodiments described in the disclosure are not intended to limit the technical spirit of the disclosure, but to illustrate, and are not limited to these embodiments.

The protection scope of the disclosure should be construed by the following claims, and all technical ideas within the scope equivalent thereto should be construed as being included in the scope of the disclosure.

The invention claimed is:

1. An optical filtering apparatus for generating a multi-wavelength image of a subject, the optical filtering apparatus comprising:
   a filter unit configured to have a plurality of sub-filter units including a first sub-filter unit through which a first wavelength band passes and a second sub-filter unit through which a second wavelength band, which is different from the first wavelength band, passes;
   a driving unit configured to drive the filter unit; and an imaging unit configured to generate the multi-wavelength image of the subject, wherein, while light generated in a light source passes through the filter unit, the filter unit filters the light such that an intensity of the first wavelength band is dominant in a first region and an intensity of the second wavelength band is dominant in a second region, wherein the driving unit drives the filter unit such that the intensity of the first wavelength band is dominant in the first region at a first time point, the intensity of the second wavelength band is dominant in the first region at a second time point, and an nth wavelength band corresponding to the plurality of sub-filter units is sequentially dominant in the first region at a subsequent nth time point, wherein the imaging unit generates the multi-wavelength image of the subject, by using one or two or more among a plurality of subject images generated at a plurality of time points, including a first subject image generated at the first time point and a second subject image generated at the second time point, and wherein the imaging unit separates a 1-1-th wavelength image corresponding to the first wavelength band and a 1-2-th wavelength image corresponding to the second wavelength band from the first subject image generated at the first time point, separates a 2-1-th wavelength image corresponding to the first wavelength band and a 2-2-th wavelength image corresponding to the second wavelength band from the second object image generated at the second time point, and then generates a first wavelength correction image corrected using the 1-1-th wavelength image and the 2-1-th wavelength image, and generates a second wavelength correction image corrected using the 1-2-th wavelength image and the 2-2-th wavelength image.

2. The optical filtering apparatus of claim 1, wherein the driving unit drives the filter unit to rotate around a rotation axis.

3. An optical filtering apparatus for generating a multi-wavelength image of a subject, the optical filtering apparatus comprising:

a filter unit configured to have a plurality of sub-filter units including a first sub-filter unit through which a first wavelength band passes and a second sub-filter unit through which a second wavelength band, which is different from the first wavelength band, passes, a driving unit configured to drive the filter unit, and an imaging unit configured to generate the multi-wavelength image of the subject, wherein, while light generated in a light source passes through the filter unit, the filter unit filters the light such that an intensity of the first wavelength band is dominant in a first region and an intensity of the second wavelength band is dominant in a second region, wherein the driving unit drives the filter unit such that the intensity of the first wavelength band is dominant in the first region at a first time point, the intensity of the second wavelength band is dominant in the first region at a second time point, and an nth wavelength band corresponding to the plurality of sub-filter units is sequentially dominant in the first region at a subsequent nth time point, wherein the imaging unit generates the multi-wavelength image of the subject, by using one or two or more among a plurality of subject images generated at a plurality of time points, including a first subject image generated at the first time point and a second subject image generated at the second time point, and wherein a gradient in which the intensity of the second wavelength band increases while the intensity of the first wavelength band decreases is included between the first region and the second region.

4. The optical filtering apparatus of claim 3, wherein the imaging unit separates the 1-1-th wavelength image corresponding to the first wavelength band and the 1-2-th wavelength image corresponding to the second wavelength band from the first subject image generated at the first time point, and then generates a first wavelength correction image and a second wavelength correction image by correcting the intensity according to the gradient.

5. The optical filtering apparatus of claim 2, wherein the driving unit drives the filter unit to generate a composite wavelength image in which the first wavelength band and the second wavelength band are uniformly exposed and mixed while the filter unit rotates one or more turns, and the imaging unit separates and generates the first wavelength correction image and the second wavelength correction image from the composite wavelength image.

6. The optical filtering apparatus of claim 1, wherein the driving unit drives the filter unit to move in one or two or more linear directions among vertical, horizontal, and oblique directions.

7. An optical filtering apparatus for generating a multi-wavelength image of a subject, the optical filtering apparatus comprising:

a filter unit configured to have a plurality of sub-filter units including a first sub-filter unit through which a first wavelength band passes and a second sub-filter unit through which a second wavelength band, which is different from the first wavelength band, passes, a driving unit configured to drive the filter unit, and wherein, while light generated in a light source passes through the filter unit, the filter unit filters the light such that an intensity of the first wavelength band is dominant in a first region and an intensity of the second wavelength band is dominant in a second region, wherein the driving unit drives the filter unit such that the intensity of the first wavelength band is dominant in the first region at a first time point, the intensity of the second wavelength band is dominant in the first region at a second time point, and an nth wavelength band corresponding to the plurality of sub-filter units is sequentially dominant in the first region at a subsequent nth time point, and wherein the first sub-filter unit includes a 1-1-th sub-filter piece and a 1-2-th sub-filter piece, the second sub-filter unit includes a 2-1-th sub-filter piece and a 2-2 sub-filter piece, and the 1-1-th sub-filter piece and the 1-2-th sub-filter piece are positioned to cross each other with the 2-1-th sub-filter piece and the 2-2-th sub-filter piece.

8. The optical filtering apparatus of claim 2, wherein the driving unit includes a gear train having a driving motor and a plurality of gears, and the number of rotations of the filter unit is greater than the number of rotations of the driving motor by the gear ratio of the gear train.

9. An optical filter method for generating a multi-wavelength image of a subject, the method comprising:

driving a filter unit using a driving unit;

filtering light generated from a light source using the filter unit configured to have a plurality of sub-filter units including a first sub-filter unit through which a first wavelength band passes and a second sub-filter unit through which a second wavelength band, which is different from the first wavelength band, passes; and generating the multi-wavelength image of the subject using the light filtered by the filter unit, wherein, in the filtering, the filter unit filters and transmits the light such that an intensity of the first wavelength band is dominant in a first region and an intensity of the second wavelength band is dominant in a second region, wherein the driving unit drives the filter unit such that the intensity of the first wavelength band is dominant in the first region at a first time point, the intensity of the second wavelength band is dominant in the first region at a second time point, and an nth wavelength band corresponding to the plurality of sub-filter units is sequentially dominant in the first region at a subsequent nth time point, and wherein the first sub-filter unit includes a 1-1-th sub-filter piece and a 1-2-th sub-filter piece, the second sub-filter unit includes a 2-1-th sub-filter piece and a 2-2 sub-filter piece, and the 1-1-th sub-filter piece and the 1-2-th sub-filter piece are positioned to cross each other with the 2-1-th sub-filter piece and the 2-2-th sub-filter piece.

\* \* \* \* \*